United States Patent
Bühren et al.

(10) Patent No.: US 6,547,791 B1
(45) Date of Patent: Apr. 15, 2003

(54) RETROGRADE TIBIAL NAIL

(75) Inventors: Volker Bühren, Murnau (DE); Thomas Wahl, Lengnau (CH); Lukas Sutter, St. Gallen (CH); Andreas Bernhard, Meinisberg (CH); Gunther O. Hofmann, Schondorf/Ammersee (DE); Oliver Gonschorek, Murnau (DE)

(73) Assignee: Stryker Trauma - Selzach AG (CH)

( * ) Notice: Subject to any disclaimer, the term of this patent is extended or adjusted under 35 U.S.C. 154(b) by 0 days.

(21) Appl. No.: 09/744,544

(22) PCT Filed: Jul. 23, 1999

(86) PCT No.: PCT/CH99/00342

§ 371 (c)(1),
(2), (4) Date: May 29, 2001

(87) PCT Pub. No.: WO00/06039

PCT Pub. Date: Feb. 10, 2000

(30) Foreign Application Priority Data

Jul. 27, 1998 (EP) .............................................. 98810717

(51) Int. Cl.$^7$ ................................................. A61B 17/72
(52) U.S. Cl. ........................ 606/62; 606/67; 623/23.32
(58) Field of Search ............................. 606/62, 63, 64, 606/67, 68; 623/23.32, 23.33

(56) References Cited

U.S. PATENT DOCUMENTS

| 4,475,545 A | * | 10/1984 | Ender | |
|---|---|---|---|---|
| 4,875,474 A | * | 10/1989 | Border | |
| 5,034,013 A | * | 7/1991 | Kyle et al. | 606/62 |
| 5,035,397 A | * | 7/1991 | Frigg | 606/67 |
| 5,041,115 A | * | 8/1991 | Frigg et al. | 606/62 |
| 5,053,035 A | * | 10/1991 | McLaren | 606/67 |
| 5,374,235 A | * | 12/1994 | Ahrens | 606/101 |
| 5,713,902 A | * | 2/1998 | Friedl | 606/64 |
| 6,123,708 A | * | 9/2000 | Kilpela et al. | 606/62 |
| 6,322,541 B2 | * | 11/2001 | Ahrens | 623/23.27 |

FOREIGN PATENT DOCUMENTS

| DE | 196 19 093 | 11/1997 |
|---|---|---|
| FR | 2 646 078 | 10/1990 |
| WO | 98 24380 | 6/1998 |

* cited by examiner

Primary Examiner—Ralph A. Lewis
(74) Attorney, Agent, or Firm—Lerner, David, Littenberg, Krumholz & Mentlik, LLP

(57) ABSTRACT

The tibia nail comprises a tube including a continuous longitudinal bore and includes a proximal anchoring portion with several cross-bores, an adjoining connecting portion which is flexurally resilient in an anterior and posterior direction, a shank adjoining it, and a distal anchoring portion. The anchoring portion is bent away with respect to the shank and has an elongated hole through which a locking screw may be placed. The tibia may be compressed by means of a compression screw inserted into a longitudinal threaded bore. The tibia nail enables retrograde implantation, which has been considered to be impossible for the tibia up to now.

20 Claims, 1 Drawing Sheet

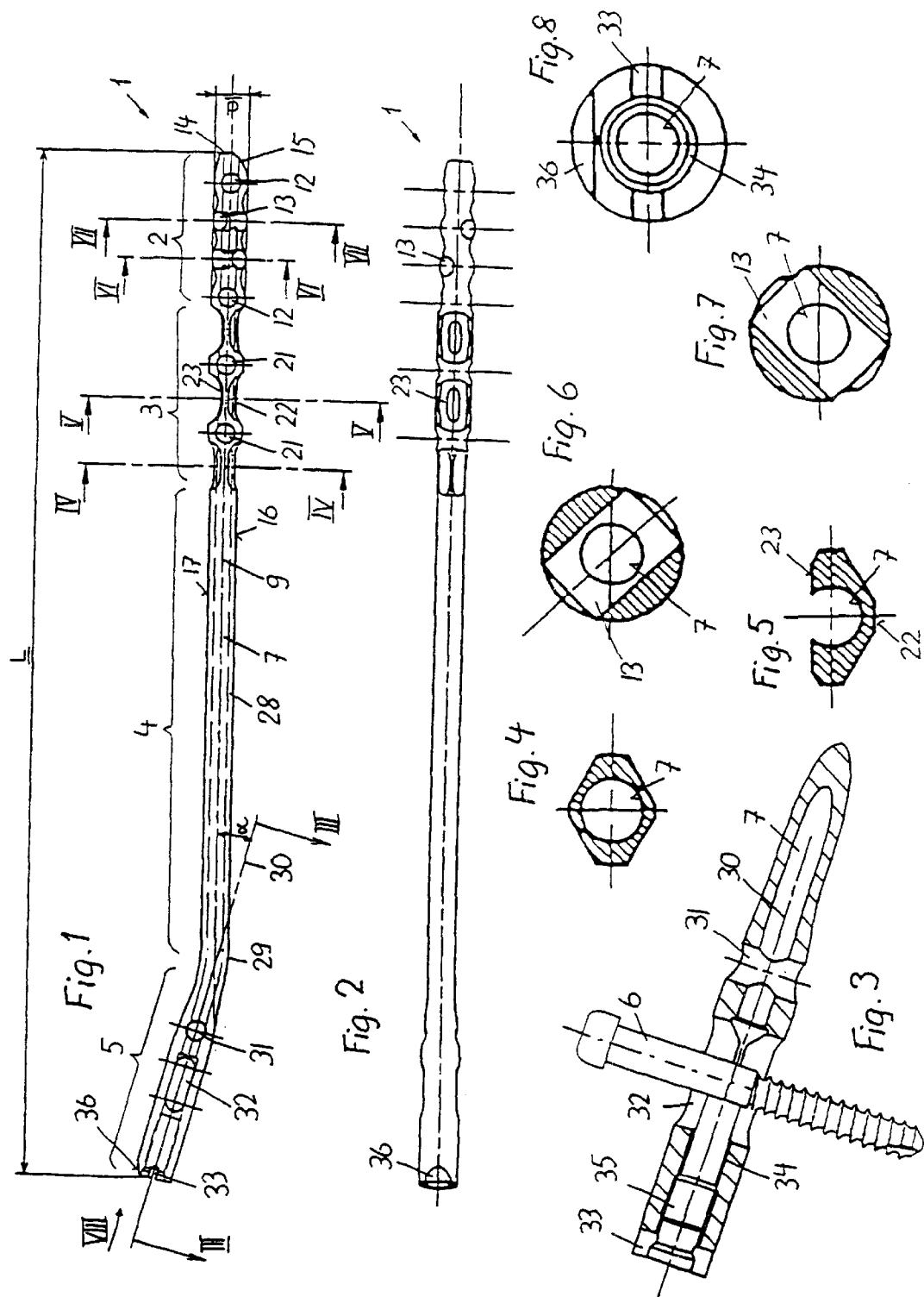

RETROGRADE TIBIAL NAIL

BACKGROUND OF THE INVENTION

The retrograde implantations of medulla nails in the femur and the humerus already are routine osteosynthetic treatments presently. In contrast, the implantation of a medulla nail into the tibia in a retrograde direction has seemed to be impossible as yet because of anatomic and implant-related technical considerations. Therefore, osteosynthetic plates, for example, have been used up to now, particularly for fractures in the proximal region of the tibia.

SUMMARY OF THE INVENTION

From FR-A-2 646 078, a bone nail has become known which also is referred to as a locking nail. The bone nail, which also can be employed as a tibia nail and, for this purpose, has a bent-off portion at its end, exhibits cross-bores in each of the end portions to receive a bone screw. The shank of the bone nail is provided with groves axially parallel thereto and with an axially extending slot in the wall of the hollow nail, which increases the resiliency of the shank altogether.

It is the object of the invention to provide a tibia nail which specifically is suited for retrograde use.

BRIEF DESCRIPTION OF THE DRAWINGS

An embodiment of the invention will now be explained with reference to the drawings. In the drawings:

FIG. 1 shows a side view of a tibia nail,

FIG. 2 shows a plan view of the nail,

FIGS. 3 through 7 show sections along lines III—III through VII—VII in FIG. 1, and FIG. 8 shows a front view in the direction of the arrow VIII in FIG. 1.

DESCRIPTION OF PREFERRED EMBODIMENTS

The intramedullary tibia nail 1 is manufactured from a bio-compatible metal. It serves for treating broken bones in the proximal portion of the tibia and for temporarily stabilizing high tibia osteotomies. The nail 1 comprises four sections: a flexurally rigid most proximal portion 2, a proximal portion 3 which is flexurally resilient in an anterior and posterior direction, a medial shank 4, and a distal flared portion 5 to receive the distal locking screws 6. The whole nail is designed cannularly (bore 7) to enable insertion by means of a target wire or guide wire. As a rule, it is configured in a rotationally symmetric way. The diameters of the individual portions 2–5 vary and typically are about 9 mm in the proximal portion 2, about 7 mm in the shank 4, and about 10 mm in the distal portion 5. The nail 1 is manufactured in a length ranging from about 200 to 400 mm with the length of the shaft 4 substantially being varied.

The most proximal portion 2 which is flexurally rigid has at least two angularly offset screw holes 12, 13 for proximal locking screws (not shown) which have their threads cut up to the screw head unlike the screws 6 of FIG. 3. At least one hole 12 is located in a medio-lateral direction. The embodiment of FIGS. 1 and 2 illustrates four holes 12, 13 with the most proximal and most distal ones being located in a medio-lateral direction and each of the two holes 13 therebetween being rotated through an angle about the axial direction of the nail, which is about 45° in the embodiment shown. The arrangement of the holes 12, 13 permits to fix several fragments at their positions in the region of the tibia plateau. The cross-section is approximately the same across the whole length in the flexurally rigid portion 2. Flexural rigidity is largest at the level of the holes 12, 13 whilst the connecting elements between the holes 12, 13 will absorb any contingent deformation. This portion 2 is configured in a rotationally symmetric manner about the longitudinal axis 9 of the nail 1. The proximal tip 14 has a skid-shaped milled area 15 of a large radius on the posterior side 16, which makes insertion easier. The radius of the milled area 15 is larger than half the diameter d of the portion 2.

The axially adjoining portion 3 has two holes 21 in a medio-lateral direction with the adjacent portions have tangential milled areas 22, 23 on the anterior side 17 and the posterior side 16, which impart greater flexibility to the nail 1 in these directions. This is particularly important because the nail 1 is introduced from the anterior side 17 of the tibia and needs to be moved around a corner in a way. In this flexurally resilient portion 3, the milled areas 23 are deeper on the anterior side 17 and intersect the bore 7 (FIG. 5) because flexion will be in the anterior direction during insertion. Flexural resiliency is significantly larger in the anterior and posterior direction than in the direction perpendicular thereto. In a realized embodiment, e.g. in the section according to FIG. 5, the area moment of insertia $I_x$=20.75 mm$^4$ about the axis which is shown horizontally and $I_y$=137.01 mm$^4$ in a direction perpendicular thereto. In the section of FIG. 4, the respective values are $I_x$=29.0 mm$^4$ and $I_y$=66.68 mm$^4$. Hence, the area moment of inertia in an anterior and posterior direction is smaller by at least a factor 2 than in a direction perpendicular thereto across at least one region of the flexurally resilient portion 3. This factor is about 6.6, i.e. between 4 and 10, in the region of the section of FIG. 5. The portion 3 is circularly cylindrical in the surroundings of the holes 21. These regions 24 serve as supports and prevent the portion 3 from kinking when under a pressure.

The shank 4 of the nail 1 which lies contiguous to the flexurally resilient portion 3 consists of a tube 28 which connects the portion 3 and the distal locking portion 5 to each other. This tube 28 typically is of a diameter between 5 and 15 mm. In the embodiment shown, the diameter was chosen so that the tube 28, when of a sufficient strength, was configured to be as soft (resilient) as possible. The distal end of this tube 28 has disposed thereon a bend 29 which passes over into the distal locking portion 5. The angle α between the axis 9 in the tube 28 and the axis 30 in the distal portion 5 may range between 5° and 30°. It is 15° in the embodiment shown. In the further course, the cross-section of the tube 28 increases in the bend 29 so that there is a steady transition from the smaller diameter of the tube 28 to the larger diameter of the distal locking portion 5.

This distal locking portion 5 has at least two cross-bores 31, 32 with the distal bore 32 being made as an elongated hole in an axial direction. These bores 31, 32 serve for receiving the distal locking bolts 6, the proximal bore 31 is for static locking bolts, the elongated hold 32 is for dynamic or compression-locking bolts 6.

The distal end has a disposed thereon a groove 33 about 3 to 5 mm in depth, which radially runs through the diameter of the nail 1. The axially bored hole of the nail 1 is largest here. Adjacent to this groove 33, a female thread 34 begins at a minor inside diameter in an axial, proximal direction and ends just in front of the most distal cross-bore 32. The distal groove 33 and the female thread 34 serve as an interface with the target apparatus during introduction, as a docking point during extraction, and for receiving a compression or closure screw 35.

The longitudinal bore of the distal locking portion, moreover, is of a larger diameter than the cannular bore 7 in the rest of the nail 1 in order that a compression screw 35 can be received, which perpendicularly pressed the bolt 6 disposed in the distal bore 32. Thus, a compression of the tibia may be achieved by turning in the screw 35. Furthermore, the distal anterior end of the nail 1 has disposed thereon a chamfer 36 which is to avoid damage to soft body parts if the nail should slightly come out of the bone because of compression.

For surgery, the patient is positioned on its back with his blood circulation blocked on his thigh and his leg covered and freely movable. Access is made via a longitudinal incision 5 to 7 cm in length at the front of the distal lower leg and the upper ankle joint. After the subcutis and the fascia are cut open the retinacula of the extensors is cut open in the longitudinal direction. The musculus extensor halluzis longus is retracted medially, the tibialis anterior vessels and the nervous peronaeus profundus are retracted laterally by means of a vein hook. The anterior cortex of the distal tibia is exposed subperiostally. Great care is taken not to open the articular capsule of the upper ankle joint.

A pricker is used to open the cortex of the distal tibia closely above the lug of the articular capsule. A guide wire having a slightly bent tip is introduced into the medullary space and, across the fracture and the osteotomy, is advanced upwards into the proximal tibia and is moved on into the emminentia intercondylaris. The medullary canal is opened by means of flexible boring shanks in a retrograde direction. The boring operation begins at a 6 mm diameter of the boring heads, is continued at 0.5 mm steps, and ends once the diameter is by 1 mm larger than the medulla nail 1 which was selected.

The isthmus of the tibia will remain the region for the firm, intromedullary fixation of the medulla nail here. The selected medulla nail 1 may be advanced by hand in most cases. If necessary, a slight hammer blows may make it easier to insert the nail 1. If resistance becomes too large during its insertion a smaller diameter is chosen for the nail. The end of the nail 1 (the chamfer 36) should be introduced so as to be somewhat deeper than the surface of the ventral tibia edge. After the compression screw 35 is inserted and compression is performed the nail 1 will then be flush with the bone surface.

The proximal locking in the tibia head is effected by the free-hand technique through the tibia head. Self-tapping 5 mm screws are preferably used for this purpose. The locking screws in the tibia head preferably are inserted from the medial to lateral points and from the ventral to dorsal points. The distal locking screws 6 are inserted by means of a target apparatus.

The advantages of the tibia nail are as follows:

It enables insertion in a retrograde direction and is specifically employed in very high tibia head fractures where a medulla nail implantation has been completely impossible as yet.

Being an intramedullary force carrier, the nail is adapted to be loaded at an early time and is by far more sturdy than in conventional types of fixation. This makes possible a better physiotherapeutic after treatment of the patient and gives him a quick recovery.

The tibia nail allows a minimally invasive operation technology.

It improves the patient's comfort.

The tibia nail in the medullary space does not impair periostal blood supply.

It avoids neuronal lesions.

The tibia nail described is primarily suited for use in proximal tibia fractures, revision osteotomies, callus distractions, segment transfer, knee joint transplantations, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A tibia nail for insertion into the medullary canal of the tibia in a retrograde manner, comprising a first anchoring portion at a proximal end thereof including at least one cross-bore for being anchored to the tibia by means of a locking bolt, a shank portion extending distally from said first anchoring portion along an axis towards a second end of said nail, and a second anchoring portion at a distal end of the nail joining the shank at angle ($\alpha$), which second anchoring portion has at least one cross-bore, the shank having a flexurally resilient connection portion adjacent the first anchoring portion the flexural resiliency of which in the first plane containing the axes of the shank and the second anchoring portion is larger than in a second plane containing the axis of the shank and being perpendicular to the first plane, the connection portion being more flexurally resilient than the first and second anchoring portions in at least one direction.

2. The tibia nail according to claim 1 wherein said nail has a continuous longitudinal bore.

3. The tibia nail according to claim 1 wherein said nail has a skid-like milled area at the free end of the first anchoring portion on the side diametrically opposed to the second anchoring portion with respect to the axis of the first anchoring portion.

4. The tibia nail according to any one of claims 1, 2 or 3 wherein the first anchoring portion has several cross-bores in different directions and wherein at least one of the cross-bores extends perpendicular to the first plane.

5. The tibia nail according to claim 1 wherein the second anchoring portion has an elongated hole as well as a screw, and wherein the second anchoring portion has an additional, cylindrical cross-bore.

6. The tibia nail according to claim 1 wherein the angle ($\alpha$) ranges from 5° to 30°.

7. The tibia nail according to claim 1 wherein the connection portion has milled areas parallel to the second plane, and wherein the milled areas from one side, specifically from the anterior side, are deeper than from another side, and the deeper milled areas intersect a longitudinal bore through said second anchoring portion.

8. The tibia nail according to claim 1 wherein the connecting portion is subdivided by supporting bodies the outside diameter of which approximately is the same than that of the first anchoring portion, and wherein the supporting bodies have further cross-bores.

9. The tibia nail according to claim 1 wherein the first anchoring portion has constricted areas between the cross-bores.

10. The tibia nail according to claim 1 wherein said nail has a chamfer on one side at the free end of the second anchoring portion.

11. The tibia nail according to claim 1 wherein the area moment of inertia about an axis perpendicular to the first axis is smaller by a factor of at least 2 than the one about an axis perpendicular to the second plane across at least one region of the flexurally resilient portion.

12. A tibial nail for insertion into the medullary canal of the tibia in a retrograde manner comprising: a first anchoring portion at a proximal end of the nail including at least one cross-bore for being anchored to the tibia by means of a locking bolt, a shank portion extending distally from said first anchoring portion along an axis towards a second end of said nail, and a second anchoring portion at a distal end of the nail joining the shank at an angle ($\alpha$) which second anchoring portion has at least another cross-bore, the nail shank having a flexurally resilient connection portion adjacent the first anchoring portion the flexural resiliency of which in the first plane containing the axis of the shank in the second anchoring portion is larger than in a second plane containing the axis of the shank and being perpendicular to the first plane wherein the connection portion has milled areas parallel to the second plane, and wherein the milled areas from an anterior side are deeper than from another other side, and the deeper milled areas intersect a longitudinal bore through said second anchoring portion.

13. A tibial nail for retrograde insertion into a tibia comprising:
    a proximal portion extending along a longitudinal axis including at least one cross-bore for receiving a locking screw;
    a tubular shank portion, said shank portion having a distal portion with a longitudinal axis extending at an angle a with respect to a longitudinal axis of the tubular portion the angle a being between 5° and 30°, the distal portion having a diameter larger than a diameter of the tubular shank portion; and
    a connecting portion connecting the proximal portion and a proximal end of said tubular shank portion, said connecting portion having a cross-section with a moment of inertia in an anterior-posterior direction less than 50% of the moment of inertia in the medial-lateral direction.

14. The tibial nail as set forth in claim 13 wherein the angle $\alpha$ is 15°.

15. The tibial nail as set forth in claim 13 wherein the proximal portion has at least two cross-bores angularly offset from one another with respect to said longitudinal axis thereof.

16. The tibial nail as set forth in claim 15 wherein the angular offset is about 45°.

17. The tibial nail as set forth in claim 13 wherein said distal portion has an elongate throughbore transverse to said axis for a cross-locking screw and a threaded axial bore for a compression screw which acts on said cross-locking screw in said bore.

18. A method for stabilizing broken bones of the tibia comprising:
    making an incision between the lower leg and the upper ankle joint and exposing the anterior cortex of the tibia;
    opening the cortex of the tibia to expose the medullary canal;
    placing a guide wire up the medullary canal of the tibia; and
    inserting a cannulated nail in the canal, said nail having a proximal portion and a distal portion connected by an intermediate portion in which the nail has a cross-section wherein the moment of inertia in the anterior-posterior direction is less than half that in the medial-lateral direction so that the nail can flex anteriorly-posteriorly on insertion and movement in the proximal direction within the tibial medullary canal.

19. The method of claim 18 further including inserting a cross-locking screw through an opening in each of said proximal and distal nail portions.

20. The method of claim 19 further including applying compression of said fracture by applying a force acting along a longitudinal axis of the nail on the cross-locking screw in said distal portion.

* * * * *

UNITED STATES PATENT AND TRADEMARK OFFICE
CERTIFICATE OF CORRECTION

PATENT NO. : 6,547,791 B1  Page 1 of 1
DATED : April 15, 2003
INVENTOR(S) : Volker Buhren et al.

It is certified that error appears in the above-identified patent and that said Letters Patent is hereby corrected as shown below:

Column 1,
Line 21, "groves" should read -- grooves --.

Column 2,
Line 1, "to fix" should read -- fixing of --.
Line 14, "have" should read -- having --.
Line 38, cancel "a".
Line 60, cancel "a" (first occurrence).

Column 3,
Line 13, "its" should read -- his --.
Line 63, "after treatment" should read -- aftertreatment --.

Column 4,
Line 59, "than" should read -- as --.

Column 5,
Line 30, "a" (second occurrence) should read -- α --.
Line 32, "a" should read -- α --.

Signed and Sealed this

Second Day of September, 2003

JAMES E. ROGAN
*Director of the United States Patent and Trademark Office*